United States Patent
Yokota

(10) Patent No.: US 7,850,606 B2
(45) Date of Patent: Dec. 14, 2010

(54) ENDOSCOPE DEVICE

(75) Inventor: Masayoshi Yokota, Tachikawa (JP)

(73) Assignee: Olympus Corporation, Tokyo (JP)

( * ) Notice: Subject to any disclaimer, the term of this patent is extended or adjusted under 35 U.S.C. 154(b) by 1140 days.

(21) Appl. No.: 11/501,978

(22) Filed: Aug. 10, 2006

(65) Prior Publication Data

US 2007/0049802 A1 Mar. 1, 2007

(30) Foreign Application Priority Data

Aug. 10, 2005 (JP) .............................. 2005-232137

(51) Int. Cl.
*A61B 1/00* (2006.01)
*A61B 1/04* (2006.01)

(52) U.S. Cl. ..................... 600/175; 600/117; 600/118

(58) Field of Classification Search .............. 600/111, 600/117, 118, 175
See application file for complete search history.

(56) References Cited

U.S. PATENT DOCUMENTS

| 4,823,283 | A * | 4/1989 | Diehm et al. ............... 715/825 |
| 6,744,477 | B2 * | 6/2004 | Meersseman ................ 348/731 |
| 6,976,954 | B2 * | 12/2005 | Takahashi .................... 600/118 |
| 6,977,670 | B2 * | 12/2005 | Takahashi et al. .............. 348/65 |
| 2002/0183590 | A1 * | 12/2002 | Ogawa ........................ 600/117 |
| 2003/0060681 | A1 * | 3/2003 | Yokota ........................ 600/117 |
| 2003/0093503 | A1 * | 5/2003 | Yamaki et al. ............... 709/220 |
| 2004/0019255 | A1 * | 1/2004 | Sakiyama .................... 600/175 |
| 2004/0030221 | A1 * | 2/2004 | Ogawa ........................ 600/175 |
| 2005/0014996 | A1 * | 1/2005 | Konomura et al. ........... 600/175 |
| 2006/0069309 | A1 * | 3/2006 | Ono ............................ 600/134 |

FOREIGN PATENT DOCUMENTS

| JP | 2001-251549 | 9/2001 |
| JP | 2004-033487 | 2/2004 |
| JP | 2004-313241 | 11/2004 |

* cited by examiner

*Primary Examiner*—John P Leubecker
(74) *Attorney, Agent, or Firm*—Scully, Scott, Murphy & Presser, P.C.

(57) ABSTRACT

An endoscope device of the present invention has an insertion portion capable of attachment and detachment of a plurality of optical adapters. The endoscope device comprises a resistor for detecting attachment and detachment of the optical adapter as well as an attachment and detachment detection portion, a ROM for storing a setting table as a specific set value for each of the plurality of optical adapters, an LCD for displaying a list of the optical adapters on the basis of the setting table, and an operation switch for selecting one optical adapter from the list of the optical adapters.

20 Claims, 9 Drawing Sheets

ENDOSCOPE DEVICE

This application claims benefit of Japanese Application No. 2005-232137 filed on Aug. 10, 2005, the contents of which are incorporated by this reference.

BACKGROUND OF THE INVENTION

1. Field of the Invention

The present invention relates to, in an endoscope device in which a plurality of types of optical adapters can be detachably mounted to an insertion portion, an endoscope device in which each portion corresponding to each adapter can be easily set in use of the optical adapter.

2. Description of the Related Art

Conventional endoscope devices include an optical-adapter type endoscope device in which a plurality of types of optical adapters can be detachably mounted to an insertion portion. These optical-adapter type endoscope devices require users to manually change setting of the optical adapter before starting observation, which makes operation of the device complicated, and manual setting change have caused a wrong setting.

In order to improve operability of the device, such a method is proposed that when a user chooses an optical adapter to be used from types of optical adapters displayed in a menu, the type of optical adapter is discriminated on the basis of the shape of a view field area of the attached optical adapter, and the setting of a measurement correction coefficient is changed (See Japanese Patent Laid-Open Publication No. 2004-33487, for example). This proposal is easy to be adapted to an endoscope with a reduced diameter, since there is no need to provide new means for discriminating the type of optical adapters.

Also, there is such a proposal to improve operability that attachment and detachment of an image-pickup lens is detected at a digital camera and an image processing condition corresponding to the image-pickup lens can be automatically set (See Japanese Patent Laid-Open Publication No. 2001-251549, for example).

Moreover, there is a proposal of an optical-adapter type endoscope device in which an optical adapter as an optical-adapter type endoscope device is provided with, for example, an IC, a resistor or the like, so that discriminating means of an endoscope main body can discriminate the optical adapter (See Japanese Patent Laid-Open Publication No. 2004-313241, for example).

SUMMARY OF THE INVENTION

An endoscope device of the present invention is an endoscope device having an insertion portion to which a plurality of different types of optical adapters can be detachably mounted, comprising an attachment and detachment detection portion for detecting the attachment and detachment of the optical adapter, a memory portion for storing setting data for information on the plurality of optical adapters in advance, a list display portion for displaying a list of the optical adapter information on a display portion on the basis of the setting data when the attachment and detachment detection portion detects attachment of the optical adapter, and a selection portion for selecting one of the plurality of optical adapters from the list.

DETAILED DESCRIPTION OF THE PREFERRED EMBODIMENTS

An embodiment of the present invention will be described below using the attached drawings.

Figure 1:
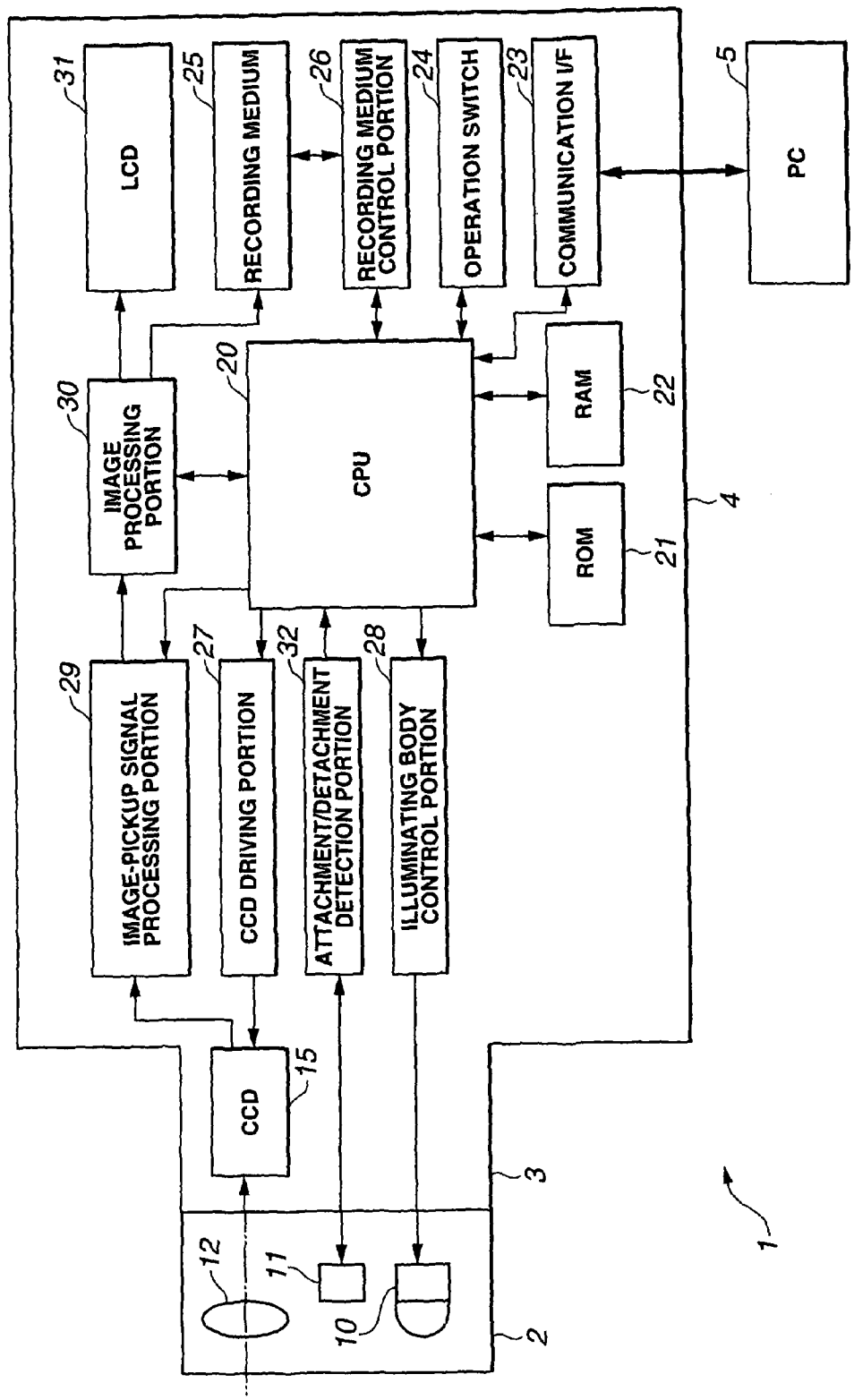
FIG. 1 is a schematic block diagram of an endoscope device according to an embodiment of the present invention.
Figure 2:
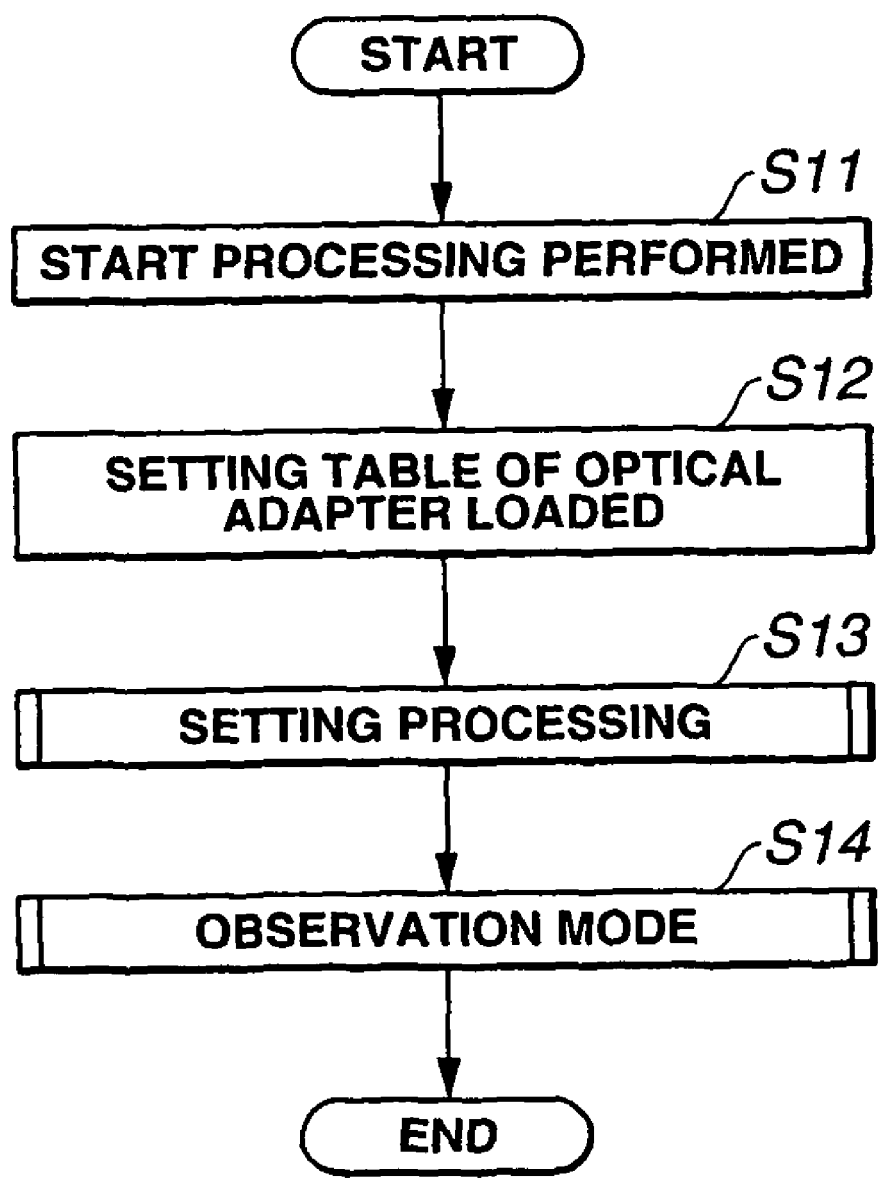
FIG. 2 is a flowchart showing an example of a flow of start processing of the endoscope device according to an embodiment of the present invention.
Figure 3:
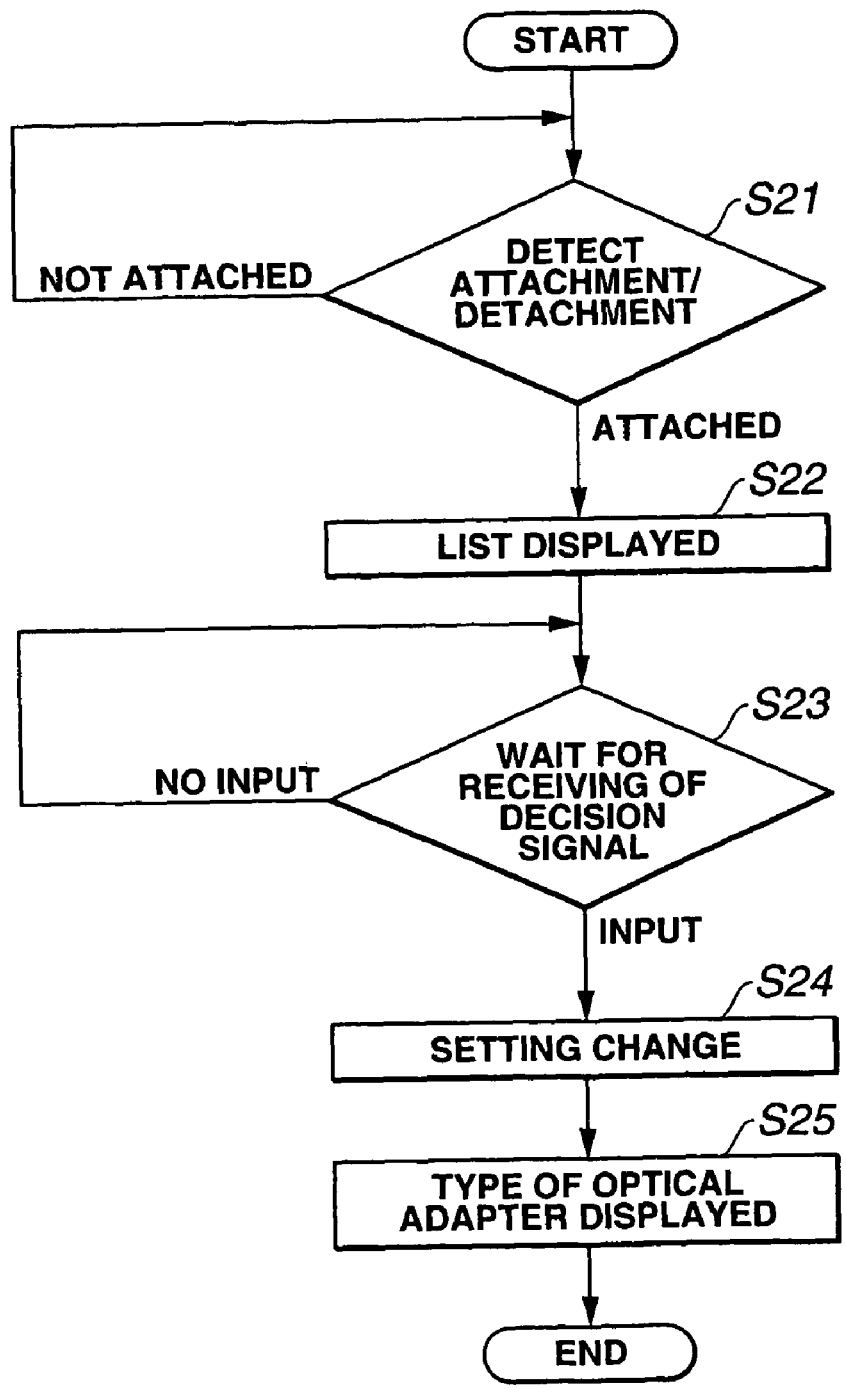
FIG. 3 is a flowchart showing an example of a flow of optical-adapter setting processing according to an embodiment of the present invention.
Figure 4:
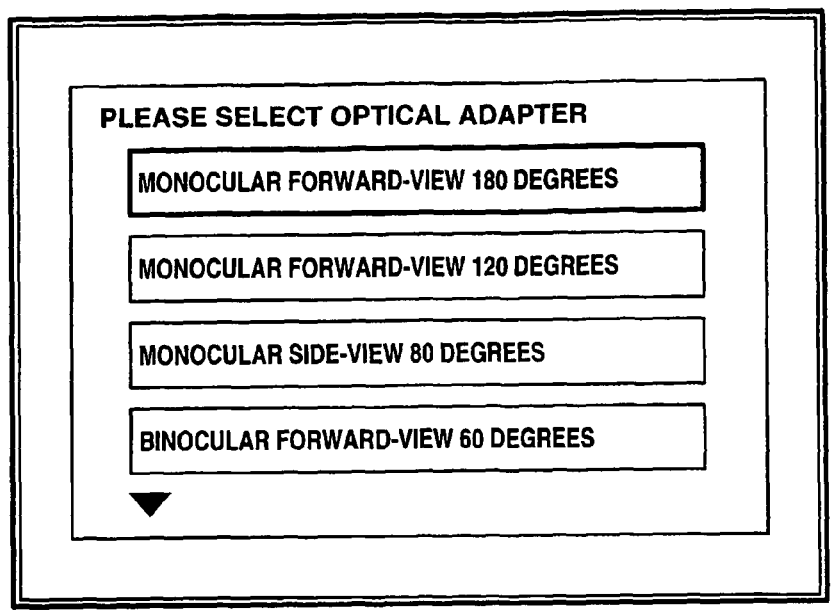
FIG. 4 is a view of an example of screen display of a list of optical adapters according to an embodiment of the present invention.
Figure 5:
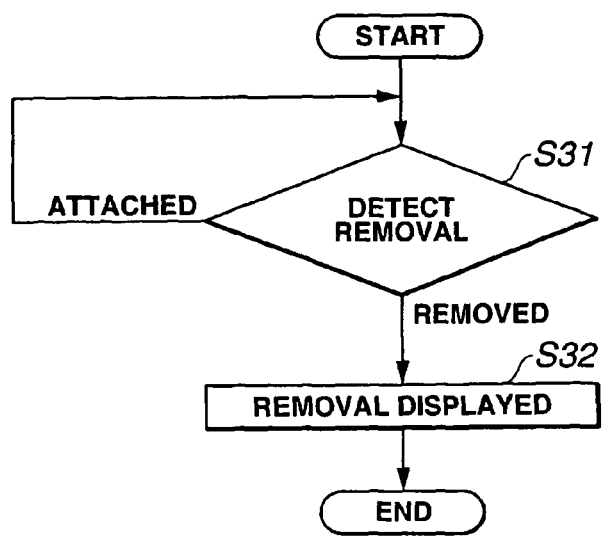
FIG. 5 is a flowchart showing an example of a flow of removal monitoring processing according to an embodiment of the present invention.
Figure 6:
FIG. 6 is a view of an example of the screen display when the optical adapter has been removed according to an embodiment of the present invention.
Figure 7:
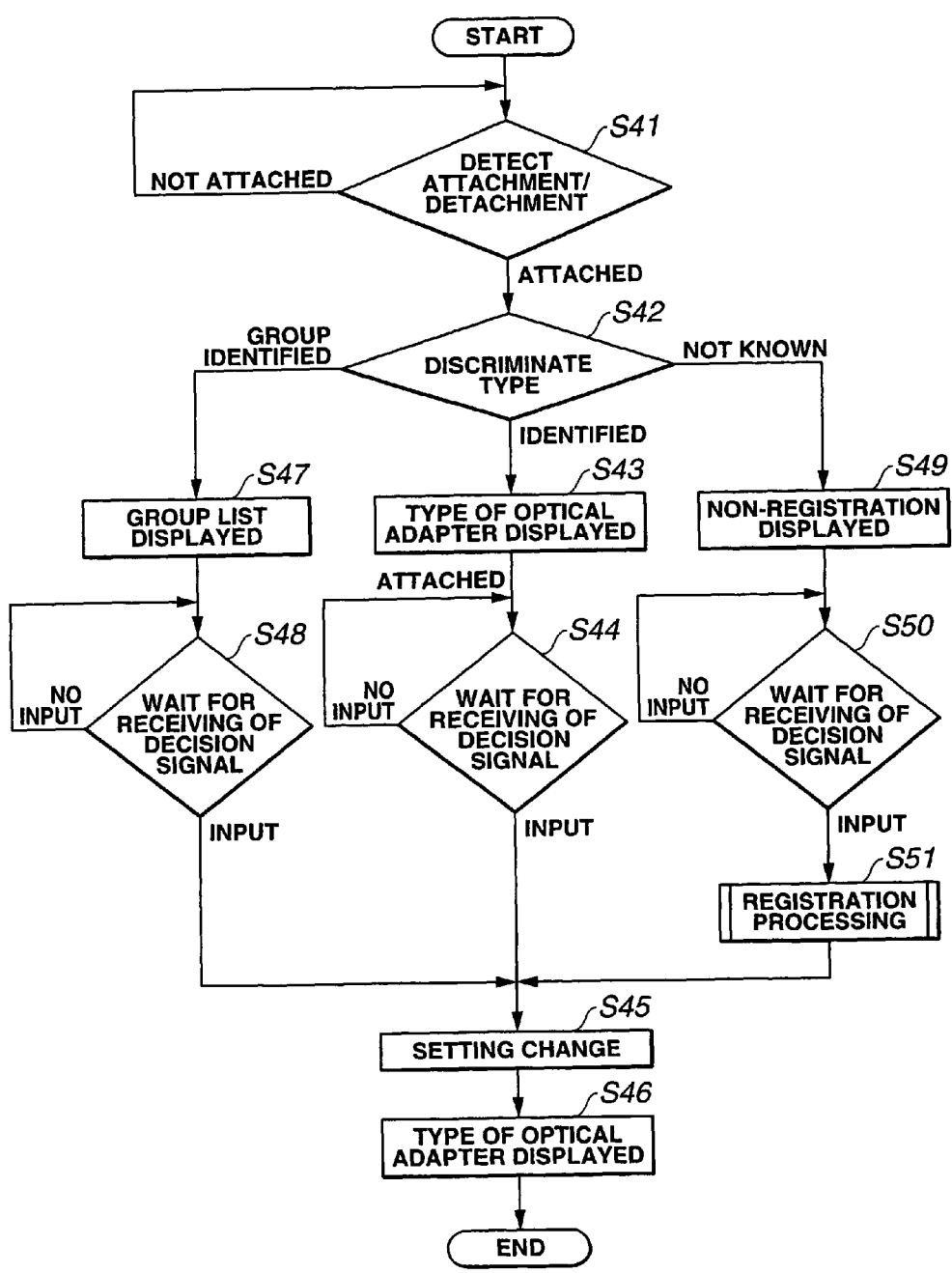
FIG. 7 is a flowchart showing an example of a flow of type detection processing of the optical adapter according to an embodiment of the present invention.
Figure 8:
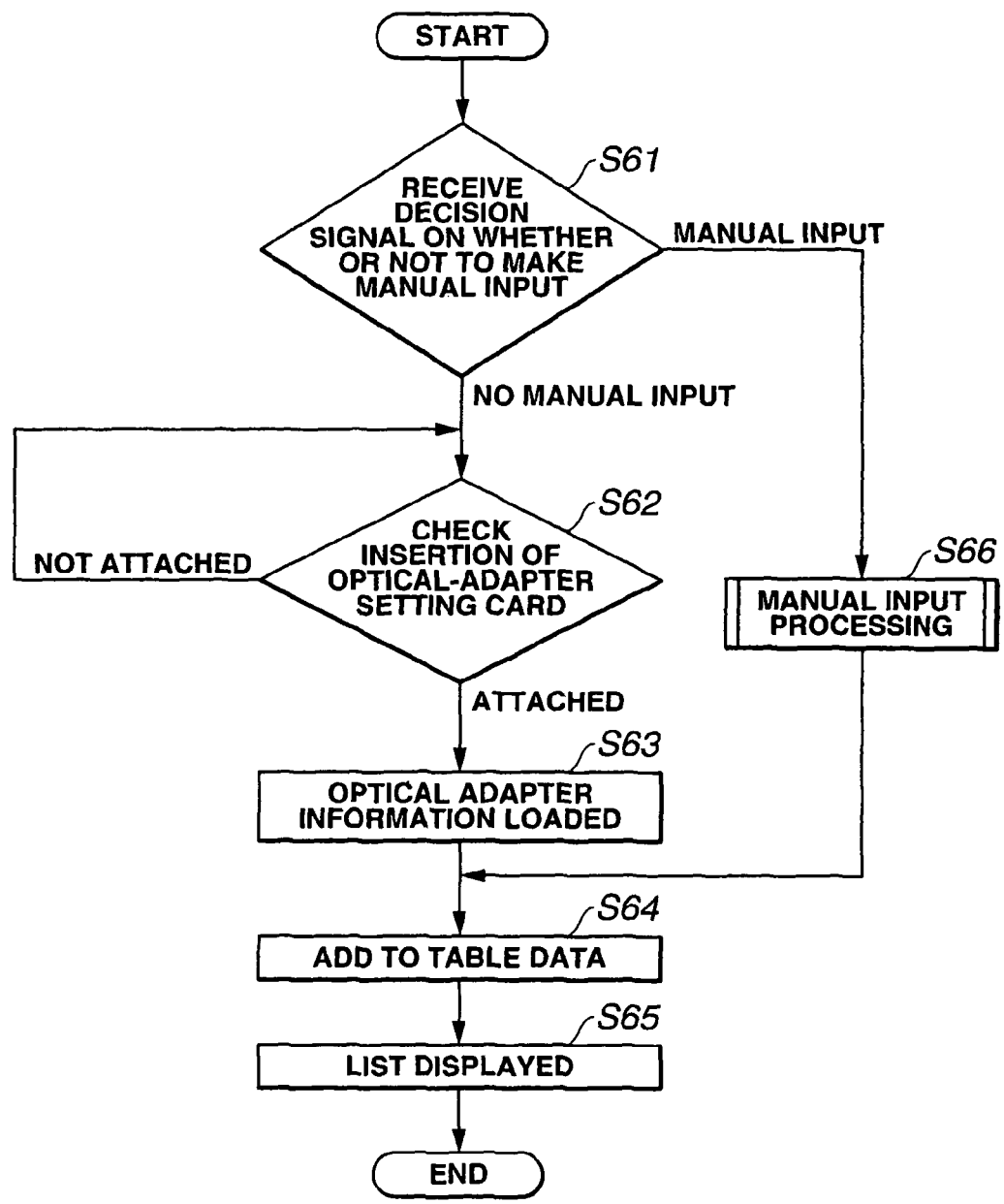
FIG. 8 is a flowchart showing an example of a flow of registration processing according to an embodiment of the present invention.
Figure 9:
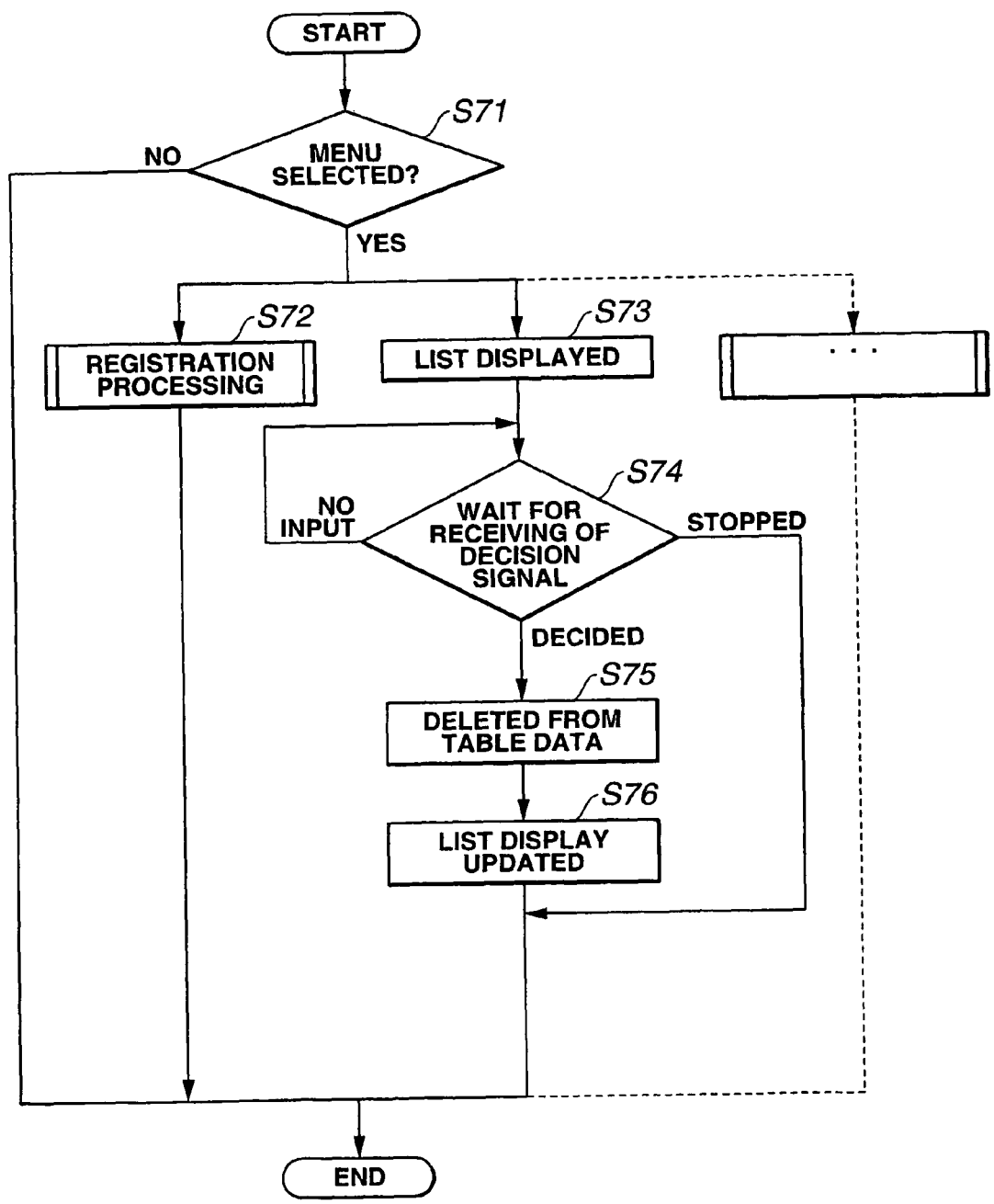
FIG. 9 is a flowchart showing an example of a flow of setting-table editing processing according to an embodiment of the present invention.
Figure 10:
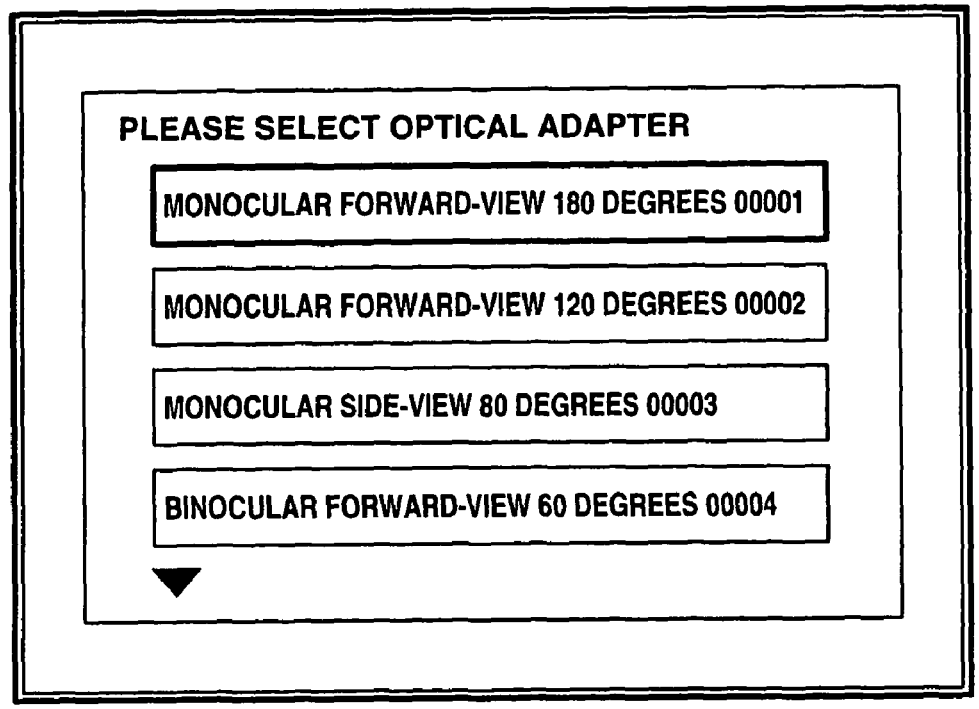
FIG. 10 is a view of an example of list display of optical adapter information including serial numbers according to an embodiment of the present invention.

FIG. 1 is a schematic block diagram of an endoscope device in an embodiment of the present invention. FIG. 2 is a flowchart showing an example of a flow of start processing of the endoscope device 1. FIG. 3 is a flowchart showing an example of a flow of optical-adapter setting processing. FIG. 4 is a view of an example of screen display of a list of optical adapters 2. FIG. 5 is a flowchart showing an example of a flow of removal monitoring processing. FIG. 6 is a view of an example of the screen display when the optical adapter has been removed. FIG. 7 is a flowchart showing an example of a flow of type detection processing of the optical adapter. FIG. 8 is a flowchart showing an example of a flow of registration processing. FIG. 9 is a flowchart showing an example of a flow of setting-table editing processing. FIG. 10 is a view of an example of list display of optical adapter information including serial numbers.

As shown in FIG. 1, the endoscope device 1 comprises a plurality of different types of optical adapters 2, an insertion tube or an insertion portion 3 capable of connection with the optical adapter 2, a main body portion 4 connected to a base end portion of the insertion portion 3, and a personal computer (hereinafter abbreviated as PC) 5.

The optical adapter 2 comprises an illuminating device 10 such as an LED for illuminating a subject, a resistor 11 for detecting attachment and detachment and type of the optical adapter 2, and a lens 12 for forming an image of reflected light from the subject (hereinafter referred to as a subject image).

At the tip end of the insertion portion 3 are arranged an image-pickup device for capturing the subject image formed by the lens 12, e.g., a charge coupled device (hereinafter abbreviated as CCD) 15 as a solid image-capturing device.

The main body portion 4 comprises a central processing unit (hereafter abbreviated as CPU) 20, a ROM 21, a RAM 22, a communication interface (hereinafter abbreviated as communication I/F) 23, an operation switch 24, a recording medium 25, a recording medium control portion 26, a CCD driving portion 27, an illuminating device control portion 28, an image-pickup signal processing portion 29, an image processing portion 30, a liquid crystal monitor (hereinafter abbreviated as LCD) 31 as a display portion, and an attachment and detachment detection portion 32. The communication I/F 23 is connected to the PC 5 via a USB, RS-232C or the like. Also, the communication I/F 23 is capable of connection to a network system such as Internet or a local area network (hereinafter abbreviated as LAN). The recording medium 25 is a portable medium such as a memory card, for example, and attached to an adapter or the like, not shown.

The following will describe one example of operation in observation by the endoscope device 1 as constructed above.

First, a user attaches the optical adapter 2 to the insertion portion 3. Then, when the user powers on the endoscope device 1, the CPU 20 executes start processing.

Next, the user performs various setting processing for endoscope observation. In general, these optical-adapter type endoscope devices are manually changed to a setting suitable for the optical adapter to be used by the user before starting observation. However, in the embodiment of the present invention, the user can make observation only by selecting the optical adapter 2 to be used from a list of the optical adapters 2 which can be used in the endoscope device 1.

And the CPU 20 sends a control signal based on the optical adapter information corresponding to the attached optical adapter 2, to each portion of the endoscope device 1 such as the illuminating device control portion 28, the CCD driving portion 27, the image-pickup signal processing portion 29, the image processing portion 30, and the recording medium control portion 26.

After that, the CPU 20 moves to an observation mode capable of endoscope observation by the user. The details of a series of the above processing from the start processing to the observation mode in the CPU 20 will be described later.

The illuminating device control portion 28 controls the illuminating device 10 according to the control signal received from the CPU 20. Also, the illuminating device 10 illuminates the subject. The subject image is formed on an image-capturing surface of the CCD 15 by the lens 12.

On the other hand, the CCD driving portion 27 drives the CCD 15 according to the control signal received from the CPU 20. The CCD 15 captures the formed subject image and sends an image-pickup signal to the image-pickup signal processing portion. And the image-pickup signal processing portion 29 performs processing such as analog/digital conversion, for example, to the image-pickup signal received from the CCD 15, according to the control signal received from the CPU 20. The image-pickup signal processing portion 29 sends a processing-completed image-pickup signal to the image processing portion 30.

Then, the image processing portion 30 performs image processing of the processing-completed image-pickup signal received from the image-pickup signal processing portion 29 to an image signal for display on the LCD 31, according to the control signal received from the CPU 20. The image processing portion 30 sends the image signal to the LCD 31 as a display portion, and the LCD 31 displays the received image signal as an image. Here, if the CPU 20 has sent a signal to record the image to the recording medium control portion 26, the image processing portion 30 sends the image signal to the recording medium 25. At the same time, the recording medium control portion 26 has the image signal recorded in the recording medium 25.

The above is the outline of the action of the endoscope device 1 in this embodiment of the present invention.

Then, the details on the processing from start processing to observation mode in the CPU 20 will be described below using the attached drawings. FIG. 2 is a flowchart showing an example of a flow of the start processing of the endoscope device 1. The processing in FIG. 2 is performed by the CPU 20. Moreover, the processing in FIG. 2 is started when the endoscope device 1 is powered on.

First, at Step S11, the CPU 20 performs the start processing. This start processing is initialization of the device or start of OS, for example.

Next, at Step S12, the CPU 20 loads a setting table including setting data as the optical adapter information from the ROM 21 as a memory portion, the recording medium 25 or the PC 5 through the communication I/F 23 into the RAM 22. This setting table information is comprised by various information on the optical adapter required for observation such as the type, field of view, required light amount or the like of the optical adapter 2 as the optical adapter information. Here, the state of the endoscope device 1 when this Step S12 has been finished is called as a standby state in the endoscope device 1.

And at Step S13, the CPU 20 performs setting processing. The details of this setting processing will be described later.

After that, at Step S14, the CPU 20 moves to the observation mode. This observation mode is a mode in which the user can make endoscope observation. In the observation mode, the CPU 20 receives an operation signal inputted by the user such as zoom, freeze or the like from the operation switch 24 or the PC 5, and sends a control signal to each portion of the endoscope device 1 on the basis of the received signal.

Then, the details of the setting processing in the CPU 20 will be described below using FIGS. 3 and 4. FIG. 3 is a flowchart showing an example of the flow of the setting processing. FIG. 4 is a view showing an example of screen display of a list of the optical adapters 2.

The processing in FIG. 3 is performed by the CPU 20. Also, the processing in FIG. 3 is a processing at Step S13 in the above mentioned FIG. 2, and the processing below starts at the transition to Step S13 in FIG. 2.

First, at Step S21, attachment and detachment of the optical adapter 2 is detected. When the optical adapter 2 is attached to the insertion portion 3, the attachment and detachment detection portion 32 generates and sends an attachment signal to the CPU 20. The CPU 20 receives the attachment signal of the optical adapter 2 from the attachment and detachment detection portion 32. When the optical adapter 2 is not attached, the processing repeats Step S21 and waits till the optical adapter 2 is attached to the insertion portion 3. When the optical adapter 2 is attached to the insertion portion 3, the processing moves to Step S22.

At Step S22, as a list display portion, the CPU 20 displays on the LCD 31 a list of the optical adapters 2 which can be used in the endoscope device 1, on the basis of the setting table read into the RAM 22. FIG. 4 shows a view of an example of the screen display of the list.

At Step S23, the CPU 20 waits for receiving of a decision signal from the operation switch 24 or from the PC 5 through the communication I/F 23, as a selection portion. This decision signal is generated when the user chooses one optical adapter to be used from the optical adapters 2 displayed in a list, by using the operation switch 24 or the PC 5. When the decision signal is not inputted, the processing repeats Step S23.

Next, at Step S24, the CPU 20 sends a control signal based on the decision signal and the setting table of the RAM 22 to each portion of the endoscope device 1. For example, if the "monocular forward-view 80 degrees" in a bold frame is selected in FIG. 4, the control signal based on the setting information of the optical adapter 2 of the "monocular forward-view 80 degrees" is sent to each portion of the endoscope device 1.

At Step S25, the CPU 20 displays the selected optical adapter 2, that is, the optical adapter information in use, on the LCD 31 through the image processing portion 30.

This finishes the setting processing, and the processing moves to the observation mode at Step S14 in FIG. 2.

In the observation mode, a removal monitoring processing is executed for monitoring all the time if the optical adapter 2 has been removed or not. Here, the removal monitoring processing will be described below using FIGS. 5 and 6. FIG. 5 is a flowchart of an example of a flow of the removal monitoring processing. FIG. 6 is a view of an example of the screen display when the optical adapter is removed.

At Step S31, the CPU 20 receives removal information from the attachment and detachment detection portion 32. If the optical adapter 2 is attached, the processing repeats Step S31, and the state where endoscopic observation is available is continued. When the optical adapter 2 is removed, the processing moves to Step S32.

At Step S32, the CPU 20 displays a message to notify that the optical adapter 2 has been removed, on the LCD 31 through the image processing portion 30. FIG. 6 shows an example of the screen display when the optical adapter 2 has been removed.

After the processing is finished, the state moves to the above-mentioned standby state of the endoscope device 1.

In the construction described above, since the list is displayed when the optical adapter 2 is attached, the user will not forget setting change of the endoscope device 1 for the optical adapter 2. Also, since the optical adapter 2 to be used is selected from the list display of the available optical adapters 2, the user can easily change the setting of the endoscope device 1.

As mentioned above, the attachment and detachment detection portion 32 detects not only attachment and detachment of the optical adapter 2 but also the type of the attached optical adapter, and it may be so constructed that the attached optical adapter 2 is displayed in the selected state at the list display, or the processing moves to Step S24 without displaying the list and the type of the optical adapter is displayed on the screen after the setting is automatically changed. Alternatively, after the type of the optical adapter is detected, only the list of the optical adapters 2 corresponding to the detection result may be displayed. Moreover, it may be so constructed that, when the optical adapter 2 not in the setting table is attached, the optical adapter information is additionally processed in the setting table. Details of the processing of the CPU 20 in that case will be described below using the attached drawings.

FIG. 7 shows a flowchart of an example of a flow of a type detection processing of the optical adapter. The processing in FIG. 7 is performed by the CPU 20. Also, the processing in FIG. 7 is started when the endoscope device 1 is in the standby state.

First, at Step S41, the CPU 20 receives an attachment and detachment type signal of the optical adapter 2 from the attachment and detachment detection portion 32. If the optical adapter 2 is not attached, the processing repeats Step S41 and waits for the optical adapter 2 to be attached to the tip end of the insertion portion. If the optical adapter 2 is attached, the processing moves to Step S42.

Then, at Step S42, the CPU 20 discriminates the type of the attached optical adapter 2 from all the types of the optical adapters 2 in the setting table read out in advance, on the basis of the attachment and detachment type signal received from the attachment and detachment detection portion 32. This attachment and detachment type signal is generated by the attachment and detachment detection portion 32 on the basis of the resistor 11.

If the attached optical adapter 2 can be identified as one optical adapter 2, the processing moves to step S43. If the optical adapter 2 can not be identified as one optical adapter but a group having the same characteristic can be identified on the basis of the optical adapter information, for example, if a plurality of optical adapter groups having the same characteristic can be identified on the basis of information such as a forward-view type, a monocular type, and the like, the processing moves to step S47. If the optical adapter 2 can not be identified and is totally unknown, the processing moves to Step S49.

First, the case where the optical adapter 2 can be identified will be described.

At Step S43, the CPU 20 displays information of the identified optical adapter 2 on the LCD 31.

Then, at Step S44, the CPU 20 waits for receiving of a decision signal on whether to use the attached optical adapter 2 or not. This decision signal is generated when the user performs confirmation operation using the operation switch 24 or the PC 5. When the decision signal is received, the processing moves to Step S45. When the decision signal can not be received, the processing repeats Step S44 and waits for receiving of the decision signal.

Then, at Step S45, the CPU 20 sends the control signal based on the optical adapter information of the optical adapter confirmed at Step 44 to each portion of the endoscope device 1.

At Step S46, the CPU 20 displays the optical adapter information of the attached optical adapter 2 on the LCD 31. After that, the processing moves to the observation mode at Step S14 in FIG. 2, and the user can make endoscopic observation.

Then, the case where the group with the same characteristic can be identified on the basis of the optical adapter information will be described. This group is a collection of optical adapter information with predetermined information of the optical adapter information matched. For example, those with specific information such as monocular, binocular matched are considered as a group.

First at Step S47, as a list display portion, the CPU 20 displays a list of optical adapter information of the group of the optical adapters 2 with the same characteristic, on the basis of the optical adapter information on the LCD 31.

And at Step S48, as a selection portion, the CPU 20 waits for receiving of a decision signal. This decision signal is generated when the user performs selection operation to select the optical adapter 2 to be used using the operation switch 24 or the PC 5. When the decision signal has not been received, the processing repeats Step S48 and continuously waits for the receiving of the decision signal.

Then, at Step S45, the CPU 20 sends a control signal based on the optical adapter information of the attached optical adapter 2 to each portion of the endoscope device 1.

At Step S46, the CPU 20 displays the information of the attached optical adapter 2 on the LCD 31. After that, the processing moves to the observation mode at Step S14 in FIG. 2, and the user can make endoscopic observation.

Next, the case where the optical adapter 2 could not be identified will be described.

First, at Step S49, the CPU 20 displays on the LCD 31 that the optical adapter 2 is not a registered optical adapter.

At Step S50, the CPU 20 waits for receiving of a decision signal. This decision signal is generated when the user performs confirmation operation to register the attached optical adapter 2 in the setting table using the operation switch 24 or the PC 5. When the decision signal is not received, the processing repeats Step S50 and continuously waits for the receiving of the decision signal.

At Step S51, the CPU 20 executes a registration processing as an editing processing. Details of this registration processing will be described later. When the registration processing is finished, the processing moves to Step S45.

Then, at Step S45, the CPU 20 sends a control signal based on the optical adapter information of the attached, that is, registered optical adapter 2 to each portion of the endoscope device 1.

At Step S46, the CPU 20 displays the optical adapter information of the optical adapter 2 on the LCD 31. After that, the processing moves to the observation mode at Step S14 in FIG. 2 and the user can make endoscopic observation.

Then, the detail of the above-mentioned registration processing of the optical adapter 2 will be described below using the attached drawings. FIG. 8 is a diagram showing a flowchart of an example of a flow of the registration processing. The following processing is performed by the CPU 20. Also, when the processing moves to Step S51 in the above FIG. 7, the processing in FIG. 8 is started.

First, at Step S61, the CPU 20 displays on the LCD 31 options on whether the optical adapter information of the attached optical adapter is to be manually inputted or not. Then the CPU 20 has the user select whether to make manual input using the operation switch 24 or the PC 5. After that, the processing moves to Step S63.

Next, if manual input is to be made, manual input processing is executed at Step S66. Though the detail of this manual input processing will be omitted, the manual input processing is a processing in which the CPU 20 has the user input the optical adapter information using the operation switch 24 or the PC 5. After that, the processing moves to Step S63.

Next, if the manual input is not to be made, at Step S62, the CPU 20 has the recording medium control portion 26 check if an optical adapter setting card of the recording medium 25 has been inserted or not. This optical adapter setting card stores the optical adapter information in advance. If the card is not inserted, the processing repeats Step S62. If inserted, the processing moves to Step S63.

At Step S63, the CPU 20 makes the recording medium control portion 26 have the optical adapter information stored in the optical adapter setting card of the recording medium 25 read by the RAM 22.

At Step S64, the CPU 20 adds the read-out optical adapter information to the setting table. This additional processing is performed by newly writing the read-out optical adapter information into the setting table.

At Step S65, the CPU 20 displays the list based on the prepared setting table on the LCD 31.

The registration processing is finished, and then, the processing moves to Step S45 in FIG. 7.

In the above described construction, even if the type of the attached optical adapter 2 can not be identified, the user can easily change the setting of the endoscope device 1 by list display by the group. By this, if at least a sensor for attachment and detachment detection is provided at the optical adapter, the list is displayed when the optical adapter is attached, and setting change will not be forgotten. Also, even if the type is discriminated, when a sensor capable of identifying all the types can not be provided, a list per group is displayed and the user is only required to select one from fewer lists. Moreover, a sensor capable of discriminating by the group can be more easily applied to an endoscope requiring a smaller diameter, because such a sensor is generally smaller in size than a sensor capable of identifying all the types. Also, even if the user wants to use the optical adapter 2 not registered in the setting table, the optical adapter 2 can be added to the setting table with a simple operation, and used thereafter.

The endoscope device 1 in the observation mode state is capable of menu display and editing of the setting table. Since the setting table can be freely edited in this way, the user can use the endoscope device 1 more easily. Details of this setting table editing processing will be described below using the attached drawings.

FIG. 9 is a flowchart of an example of a flow of the setting table editing processing. The processing in FIG. 9 is performed by the CPU 20. Also, the processing in FIG. 9 is executed when the menu is displayed using the operation switch or the PC in the observation mode state of the endoscope device 1. In this state, a top menu screen is displayed.

First, at Step S71, the CPU 20 determines the selected processing. Here, the top menu displays options for registration, deletion of the optical adapter 2, setting relating to image-capturing state, not shown, such as gain change, color inversion, shutter speed and the like or measurement and the like. And the CPU 20 receives a selection signal. This selection signal is generated when the user performs selection operation to select one from the menu using the operation switch 24 or the PC 5.

When the menu display is stopped, Step S71 results in NO and the state returns to the observation mode. When the decision signal showing registration of the optical adapter is received, the processing moves to Step S72 and moves to Step S61 in the above FIG. 8 so as to execute the registration processing. When the selection signal showing deletion of the optical adapter is received, the processing moves to Step S73.

At Step S73, the CPU 20 displays the list of the registered optical adapters 2 on the LCD 31.

At Step S74, the CPU 20 waits for receiving of a decision signal. This decision signal is generated when the user performs the selection operation to select the optical adapter 2 to be deleted using the operation switch 24 or the PC 5. When the decision signal is not received, the processing repeats Step S74 and waits for the receiving of the decision signal.

At Step S75, the CPU 20 deletes the optical adapter information of the optical adapter 2 to be deleted from the setting table.

At Step S76, the CPU 20 displays the list of new optical adapters 2 on the LCD 31.

Then, the setting table editing processing is finished. Also, if stopping the deletion processing is selected at Step S74, this processing is finished similarly.

In the above described construction, the setting table of the optical adapters used by the user can be easily edited using the menu operation.

When the optical adapter 2 requiring individual identification is to be used as the optical adapter 2 for measurement, as shown in FIG. 10, the optical adapter information including a serial number of the optical adapter 2 is displayed. Alternatively, the type of the optical adapter 2 including the serial number may be discriminated by the attachment and detachment detection portion 32.

In this way, in the case of the optical adapter type endoscope device, many types of the optical adapters 2 may be handled, and particularly if individual identification is needed, the number is extremely large. However, since the number of optical adapters 2 actually used by the user is limited, if only those required by the user are selected using the registration and deletion function of the optical adapter 2, unnecessary optical adapters 2 are not displayed in the list display and the selection of the optical adapter 2 can be made more easily.

Also, in this embodiment, the setting table may use various recording media such as a detachable recording media, portable media and the like other than the ROM 21. As the optical adapter setting card in which the optical adapter information to be registered is written, a recording medium such as a CF memory card and PCMCIA memory card may be used. Moreover, the optical adapter information may be obtained from the PC 5 connected through the communication I/F 23 and a network such as LAN, and be added to the setting table.

In this embodiment, the CPU 20 may be so constructed that it does not identify the single attached optical adapter 2 but discriminates only a group. In that case, the resistor and the attachment and detachment detection portion 32 in the optical adapter 2 can be constructed by smaller resistors or circuits than the case where a single optical adapter is identified. As a result, contribution can be made to size reduction of the optical adapter 2 and the endoscope device 1. It is needless to say that easiness of operation can be maintained by the list display of the optical adapter information.

Moreover, in this embodiment, the optical adapter information may include optical adapter group information freely inputted by the user. In this case, by adding information such as a group of optical adapters frequently used by the user to the optical adapter information, the optical adapter can be selected more easily and conveniently.

Also, a plurality of users may use the setting table for each of the users. In that case, by executing the setting table editing processing for each of the users, the setting table is prepared and used for each of the users. As a result, the plurality of users can easily make observation using a single endoscope device.

In this embodiment, the list of the optical adapter information is displayed on the LCD 31, but the list may be displayed on other display media such as a display device connected to the PC 5, a display device separately connectable to the endoscope device 1 or the like, for example.

In this embodiment, the CPU 20 may control, for example, driving of an illuminating device, illumination light amount, a gain value of an image-pickup signal or the like from the discrimination result of the optical adapter 2. Also, the CPU 2 may perform calculation processing such as for aberration correction coefficient, focal length and measurement, for example, from the discrimination result of the optical adapter 2.

In this embodiment, operation and input by the user are not limited to the operation switch 24 and the PC 5 but various devices may be used. In that case, the user performs the operation and input by connecting a device for operation and input to the communication I/F 23.

Moreover, in this embodiment, the illuminating device 10 is arranged inside the optical adapter 2, but the illuminating device 10 may be arranged inside the main body portion 4 so that the illumination light illuminates a subject through a light guide cable. In that case, further size reduction of the optical adapter 2 is made possible.

As mentioned above, this embodiment can be applied to an optical-adapter type endoscope device in which an optical adapter is attached to a tip end portion of an endoscope with a reduced diameter, and can realize an optical-adapter type endoscope device which can easily set various settings suitable for an attached optical adapter. Moreover, an optical-adapter type endoscope device with good operability and in which optical adapter information can be freely edited can be realized.

The present invention is not limited to the above-mentioned embodiment but variation without changing the gist of the present invention is possible.

What is claimed is:

1. An endoscope device having an insertion portion capable of attachment and detachment of different types of a plurality of optical adapters, comprising:
    an attachment and detachment detection portion for detecting the attachment and detachment of the optical adapter and for detecting a type of the optical adapter; and
    a display portion for displaying, when an optical adapter for measurement is attached to the insertion portion, optical adapter information of the optical adapter for measurement on the basis of a detecting result by the attachment and detachment detection portion before a measurement process using an image taken through the optical adapter for measurement is performed.

2. The endoscope device according to claim 1, further comprising a memory portion for storing setting data for information of the plurality of optical adapters in advance.

3. The endoscope device according to claim 2, wherein the display portion displays a list of the optical adapter information on the basis of the setting data.

4. The endoscope device according to claim 3, wherein the list contains the information of the optical adapter for measurement.

5. The endoscope device according to claim 3, wherein the display portion displays the list in a state that the attached optical adapter is indicated at the list on the basis of the detecting result.

6. The endoscope device according to claim 3, further comprising a selection portion for selecting one of the plurality of optical adapters from the list.

7. The endoscope device according to claim 3, further comprising an editing portion for executing editing processing of the setting data.

8. The endoscope device according to claim 7, wherein the editing processing by the editing portion includes at least one of addition or deletion of the setting data.

9. The endoscope device according to Claim 3, wherein the display portion provides the plurality of optical adapters with the same characteristic as a group, on the basis of the optical adapter information, and displays the optical adapter information of the plurality of optical adapters belonging to the group.

10. The endoscope device according to claim 2, wherein the memory portion is a recording medium.

11. The endoscope device according to claim 2, further comprising an editing portion for executing editing processing of the setting data.

12. The endoscope device according to claim 11, wherein the editing processing by the editing portion includes at least one of addition or deletion of the setting data.

13. The endoscope device according to claim 12, wherein the display portion provides the plurality of optical adapters with the same characteristic as a group, on the basis of the optical adapter information, and displays the optical adapter information of the plurality of optical adapters belonging to the group.

14. The endoscope device according to claim 13, wherein the setting data comprises optical adapter information for identifying the plurality of optical adapters by the group.

15. The endoscope device according to claim 12, wherein the memory portion is a recording medium.

16. The endoscope device according to claim 1, wherein the display portion displays a message indicating the detachment of the optical adapter when the optical adapter is detached.

17. The endoscope device according to claim 1, further comprising a resistor provided in the optical adapter,
wherein the resistor is corresponding to the type of the optical adaptor.

18. The endoscope device according to claim 1, further comprising a circuit provided in the optical adapter,
wherein the circuit is corresponding to the type of the optical adaptor.

19. A method performed using an endoscope device, the method comprising:
detecting attachment of an optical adapter for measurement to an insertion portion of the endoscope device;
detecting a type of the optical adapter using a processing unit of the endoscope device;
displaying optical adapter information of the optical adapter on the basis of a result of the type detecting step before a performing measurement step on a display of the endoscope device; and
performing measurement using an image taken through the optical adapter.

20. The method according to claim 19, further comprising;
detecting detachment of the optical adapter from the insertion portion; and
displaying a message indicating the detachment of the optical adapter after the detachment detecting step on the display.

* * * * *